(12) United States Patent
Kwon et al.

(10) Patent No.: US 8,329,434 B2
(45) Date of Patent: Dec. 11, 2012

(54) ENHANCED PROMOTER AND METHOD FOR PRODUCING L-LYSINE USING THE SAME

(75) Inventors: Do Hyun Kwon, Ulsan (KR); Hyung Joon Kim, Seoul (KR); Jae Woo Jang, Suwon-si (KR); Jun Ok Moon, Seoul (KR); Sang Jo Lim, Incheon (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 13/037,790

(22) Filed: Mar. 1, 2011

(65) Prior Publication Data

US 2011/0217741 A1 Sep. 8, 2011

(30) Foreign Application Priority Data

Mar. 5, 2010 (KR) .................. 10-2010-0020140

(51) Int. Cl.
*C12P 13/08* (2006.01)
*C12N 15/77* (2006.01)
*C12N 1/21* (2006.01)
*C07H 21/04* (2006.01)

(52) U.S. Cl. ................ 435/115; 435/252.32; 435/320.1; 536/24.1

(58) Field of Classification Search .................. None
See application file for complete search history.

(56) References Cited

U.S. PATENT DOCUMENTS

| 6,221,636 B1 | 4/2001 | Hayakawa et al. |
| 6,746,855 B2 | 6/2004 | Kreutzer et al. |
| 7,608,437 B2 | 10/2009 | Asakura et al. |
| 2002/0086370 A1 | 7/2002 | Otsuna et al. |
| 2006/0003424 A1 | 1/2006 | Asakura et al. |
| 2009/0215133 A1 | 8/2009 | Bathe et al. |

FOREIGN PATENT DOCUMENTS

| WO | WO 2006/071099 A1 | 7/2006 |
| WO | WO 2008/033001 A1 | 3/2008 |
| WO | WO 2009/096689 A2 | 8/2009 |
| WO | WO 2009/096690 A2 | 8/2009 |

OTHER PUBLICATIONS

Blombach, B., et al., "Acetohydroxyacid Synthase, a Novel Target for Improvement of L-Lysine Production of *Corynebacterium glutamicum*," *Appl. Environ. Microbiol.* 75(2):419-27, Amercan Society for Microbiology, United States (2009).

Pátek, V., et al., "Promoters for *Corynebacterium glutamicum*: cloning, molecular analysis and search for a consensus motif," *Microbiology* 142:1297-1309, Society for General Microbiology, United Kingdom (1996).

"*Corynebacterium glutamicum* ATCC 13032 DNA, Complete Genome," NCBI Entrez, GenBank Database Report, Accession No. BA000036, Nakagawa, S., Entry Date: May 24, 2002, 1 page.

International Search Report for International Application No. PCT/KR2011/000012, Korean Intellectual Property Office, Daejeon, Republic of Korea, mailed on Sep. 27, 2011, 5 pages.

Extended European Search Report, which includes the European Search Report and European Search Opinion, for EP 11 00 1256, European Patent Office, Munich, Germany, mailed on Aug. 24, 2011, 6 pages.

*Primary Examiner* — Tekchand Saidha
*Assistant Examiner* — Md. Younus Meah
(74) *Attorney, Agent, or Firm* — Sterne, Kessler, Goldstein & Fox P.L.L.C.

(57) ABSTRACT

The present invention provides a nucleic acid molecule having enhanced promoter activity, which is operably linked to a gene encoding aspartate aminotransferase and derived from *Corynebacterium glutamicum*, a vector comprising the nucleic acid molecule, a transformant transformed with the vector, and a method for producing L-lysine using the transformant.

17 Claims, 4 Drawing Sheets

ENHANCED PROMOTER AND METHOD FOR PRODUCING L-LYSINE USING THE SAME

REFERENCE TO SEQUENCE LISTING SUBMITTED ELECTRONICALLY

The content of the electronically submitted sequence listing, file name: sequencelisting_ascii.txt; size: 7,325 bytes; and date of creation: Mar. 1, 2011, filed herewith, is incorporated herein by reference in its entirety.

TECHNICAL FIELD

The present invention relates to an enhanced promoter and a method for producing L-lysine using the same.

BACKGROUND ART

Coryneform bacteria are industrial microorganisms that have been widely used to produce amino acids and various nucleic acids. Coryneform bacteria are gram-positive bacteria that are used to produce chemical substances having various industrial applications in the areas of animal feed, drugs, food processing, or the like, which include amino acids such as L-lysine, L-threonine, L-arginine, and glutamic acid, and various nucleic acids, and require biotin for growth. They are characterized by snapping division, and having little tendency to degrade produced metabolites. Such coryneform bacteria are exemplified by the genus *Corynebacterium* including *Corynebacterium glutamicum*, the genus *Brevibacterium* including *Brevibacterium flavum*, *Arthrobacter* sp., and *Microbacterium* sp.

As one of L-amino acids, L-lysine is commercially used as an animal feed supplement, because of its ability to improve the quality of feed by increasing the absorption of other amino acids, in human medicine, particularly as ingredients of infusion solutions, and in the pharmaceutical industry. Therefore, the industrial production of lysine has become an economically important industrial process.

To improve the lysine production efficiency, the enzymatic activity of the biosynthetic pathway has been increased by amplifying individual genes in the lysine biosynthetic pathway or modifying their promoters. *Corynebacterium* strains anchoring enhanced genes involved in lysine biosynthesis and methods of producing L-lysine are well known in the art. For example, U.S. Pat. No. 6,746,855 discloses *corynebacteria* strains with an enhanced lysE gene (lysine export carrier gene), to which genes selected from the group consisting of a dap A gene, a lysC gene, a pyc gene and a dapB gene are additionally introduced, and a method for the production of L-lysine by cultivating the strains. In addition, U.S. Pat. No. 6,221,636 discloses a coryneform bacterium carrying a recombinant DNA comprising a DNA sequence coding for aspartokinase, in which the feedback inhibitory activity of L-lysine and L-threonine is substantially desensitized, and a DNA sequence coding for a diaminopimelate decarboxylase. US Pat. Application No. 20060003424 discloses a method of producing L-amino acid using coryneform bacteria which has an improved enzymatic activity by modification of the promoter for GDH gene, CS gene, ICDH gene, pDH gene, or ACO-producing gene to make it close to a consensus sequence.

To develop high titer strains from such coryneform bacteria by genetic engineering or metabolic engineering, the expression of genes involved in several metabolic pathways should be selectively regulated in coryneform bacteria. To this end, it is important to regulate the activity of a promoter, which is a regulatory region and recruits RNA polymerase to initiate transcription of DNA molecule.

Until now, there is no report of coryneform bacteria which has a high expression rate by improvement of the promoter of aspartate aminotransferase (EC; 2.6.1.1; aspB) gene which is considered to play an important role in the supply of a lysine precursor, aspartate in the lysine biosynthetic pathway.

DISCLOSURE

Technical Problem

Therefore, the present inventors have made an effort to increase the expression rate by improvement of the promoter of the aspB gene. Finally, they provide a microorganism belonging to the genus *Corynebacterium*, which shows an aspartate aminotransferase activity greater than its endogenous activity by improvement of the aspB promoter on the *Corynebacterium* chromosome through base substitution and introduction of the improved promoter, thereby completing the present invention.

Technical Solution

It is an object of the present invention to provide a nucleic acid molecule having an enhanced promoter activity, which is derived from *Corynebacterium glutamicum*.

It is another object of the present invention to provide a vector comprising the nucleic acid molecule having an enhanced promoter activity.

It is still another object of the present invention to provide a transformant which is transformed with the vector.

It is still another object of the present invention to provide a method for producing lysine, comprising the step of culturing the transformant.

Advantageous Effects

The nucleic acid molecule having an enhanced promoter activity according to the present invention, which is operably linked to the aspB gene and derived from *Corynebacterium glutamicum*, shows a higher promoter activity than the wild-type, and therefore, improves the aspartate aminotransferase activity, leading to the increased production efficiency of lysine.

BEST MODE

In one aspect to achieve the above objects, the present invention relates to a nucleic acid molecule having an enhanced promoter activity, which has any one base sequence selected from the group consisting of SEQ ID NOs. 2, 3 and 4.

In one preferred embodiment, the base sequence may be operably linked to a gene coding for aspartate aminotransferase, and may be derived from the genus *Corynebacterium*.

The term "promoter", as used herein, indicates a DNA region to which a polymerase binds to initiate gene transcription, namely, an untranslated nucleic acid sequence, usually found upstream of a coding sequence, providing a recognition site for RNA polymerase, and located upstream of an mRNA transcription initiation site, to the 5' direction.

The *Corynebacterium glutamicum* nucleic acid molecule having promoter activity of the present invention is operably linked to the gene coding for aspartate aminotransferase. The gene coding for aspartate aminotransferase is an aspB gene, which is a major gene involved in the pathway of lysine biosynthesis in the genus *Corynebacterium*. Aspartate aminotransferase plays an important role in the supply of the precursor for lysine biosynthesis, aspartate by catalyzing the reaction of transferring amino groups from glutamate to oxaloacetate. Therefore, when the activity of aspartate aminotransferase increases, the precursor for lysine biosynthesis, aspartate is increased, leading to increased lysine biosynthesis. In addition, the term "operably linked", as used herein, means that the nucleic acid sequence having a promoter activity of the present invention is functionally linked to the gene encoding aspartate aminotransferase to initiate and mediate transcription of the coding sequence, indicating that the nucleic acid sequence having a promoter activity of the present invention is operably linked to the aspB gene to control the transcriptional activity of the operon gene.

Up to now, the transcriptional start site initiating gene transcription on the promoter of aspB gene has not been yet identified.

Accordingly, in one specific Example, the present inventors performed 5'-RACE (Rapid Amplification of 5' cDNA Ends) technique (Sambrook, J., Russell, D. W. Molecular Cloning: a laboratory manual 3rd ed. 8.54) in order to identify the transcriptional start site of aspB gene. 5'-RACE is a method for cloning an unknown 5'-upstream region using a known mRNA, and was performed using a 5'-Full Race core set (Cat. No. 6122) available from Takara. As a result, the transcriptional start site of aspB gene was identified as G found 72 bp upstream of the initiation codon, ATG.

The identified transcriptional start site was numbered as +1, and the promoter consensus sequence region was selected for improvement.

The nucleic acid sequence having promoter activity of the present invention is an improved aspB promoter of *Corynebacterium glutamicum*, and is characterized in that it has a higher promoter activity than the wild-type promoter. Improvement of the promoter activity may be performed by any method known in the art without limitation. Preferably, mutation in the promoter sequence of aspB gene of *Corynebacterium glutamicum* may be induced by deletion, insertion, non-conservative or conservative substitution, or combinations thereof for improvement of the promoter.

The promoter nucleic acid molecule of the present invention may be isolated or prepared using a standard molecular biology technique. For example, it may be isolated by PCR using proper primer sequences. Also, it may be prepared by a standard synthesis technique using an automated DNA synthesizer.

In one specific Example, the present inventors acquired a base sequence (SEQ ID NO. 1) containing the promoter region of aspB gene (NCBI Registration No. NCgl0237) based on GenBank of the US National Institutes of Health (NIH) and then, on the basis of this, they synthesized eight primers (SEQ ID NOs. 10 to 17). Subsequently, PCR was performed using the chromosomal DNA of *Corynebacterium glutamicum* ATCC13032 as a template and the above primers to obtain the nucleic acid molecule according to the present invention, which contains the promoter having modified sequence (SEQ ID NOs. 2, 3 and 4).

The nucleic acid molecule having *Corynebacterium glutamicum* promoter activity of the present invention is useful as a promoter for gene expression of prokaryotic cells, in particular, *E. coli* or coryneform bacteria. The term "coryneform bacteria", as used herein, include microorganisms belonging to the genus *Corynebacterium* or *Brevibacterium*, *Arthrobacter* sp. and *Microbacterium* sp. Such coryneform bacteria include *Corynebacterium glutamicum* ATCC 13032, *Corynebacterium thermoaminogenes* FERM BP-1539, *Brevibacterium flavum* ATCC 14067, *Brevibacterium lactofermentum* ATCC 13869, and L-amino acid-producing mutants or strains prepared therefrom, for example *Corynebacterium glutamicum* KFCC 10881 and *Corynebacterium glutamicum* KFCC 11001, and preferably *Corynebacterium glutamicum* KFCC 10881, but are not limited thereto.

In still another aspect, the present invention relates to a vector comprising the nucleic acid molecule having an enhanced promoter activity.

The term "vector", as used herein, refers to a DNA construct that contains a DNA sequence which is operably linked to a suitable control sequence to expresses a target gene in a suitable host. Such control sequences may include a promoter to direct transcription, a certain operator sequence to control such transcription, a sequence encoding a suitable ribosome-binding site on the mRNA, and a sequence to control termination of transcription and translation.

The vector used in the present invention is not particularly limited, and may be any vector known in the art, as long as it is replicable in the host. For example, the vector may be a plasmid, a phage particle, or simply a potential genome insert, and is preferably a pECCG122 vector (Kab-Su Noh et al., Kor. Jour. Microbiol. July. 1991 p. 149-154), but is not limited thereto. Once transformed into a suitable host, the vector may replicate and function independently of the host genome, or may, in some cases, integrate into the genome itself.

Specifically, the vector of the present invention is introduced into a host cell to generate homologous recombination between the nucleic acid molecule sequence having promoter activity within the vector and the promoter region of the endogenous aspB gene on the host genome, and thus it may integrate into the genome. Therefore, the vector of the present invention may further include a selection marker to ensure the chromosomal insertion. The selection marker is used for the selection of transformed cells, namely used to ensure the insertion of a target gene, and may include markers providing selectable phenotypes, such as drug resistance, auxotrophy, resistance to cytotoxic agents, or surface protein expression. Only cells expressing the selection marker are able to survive or to show different phenotypes under the environment containing the selective agent, and thus the transformed cells can be selected. Preferably, the vector of the present invention may include a lacZ gene.

Figure 1:
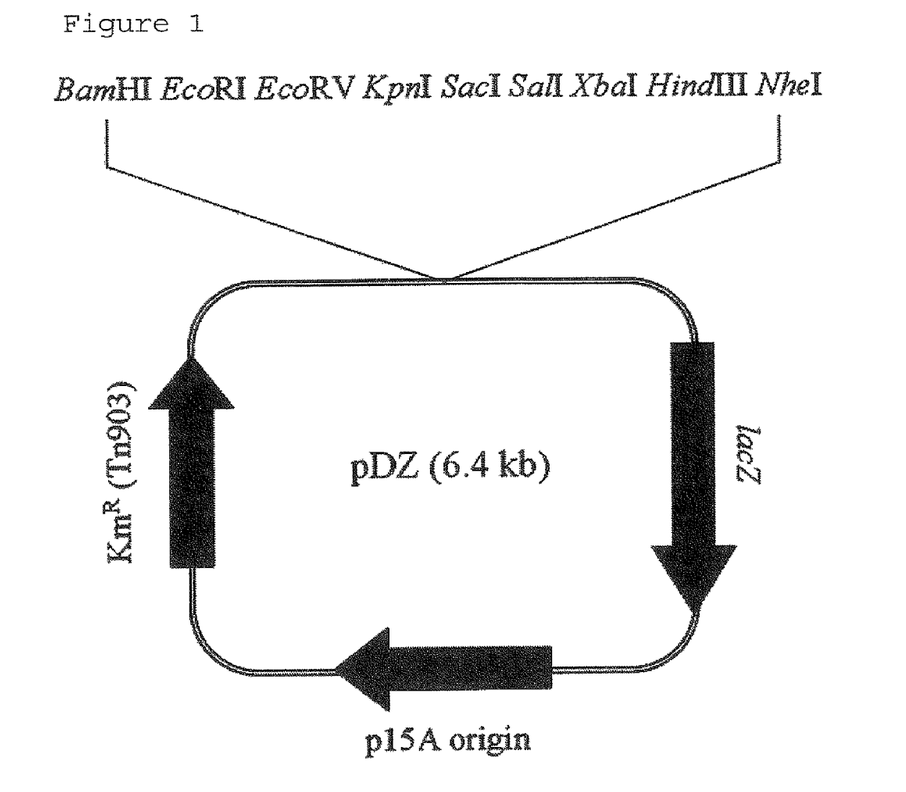
FIG. 1 shows a vector pDZ for insertion into *Corynebacterium* chromosome.
Figure 3:
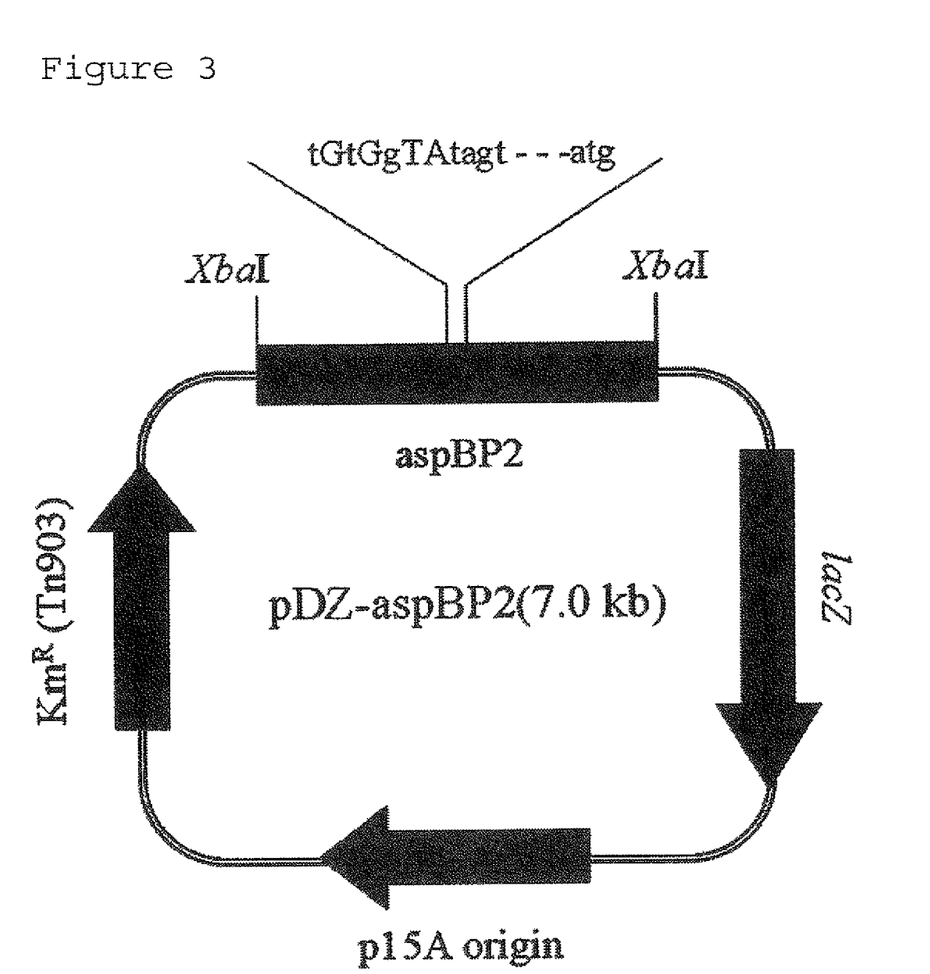
FIG. 3 shows a vector pDZ-aspBP2 for base substitution into *Corynebacterium*.
Figure 4:
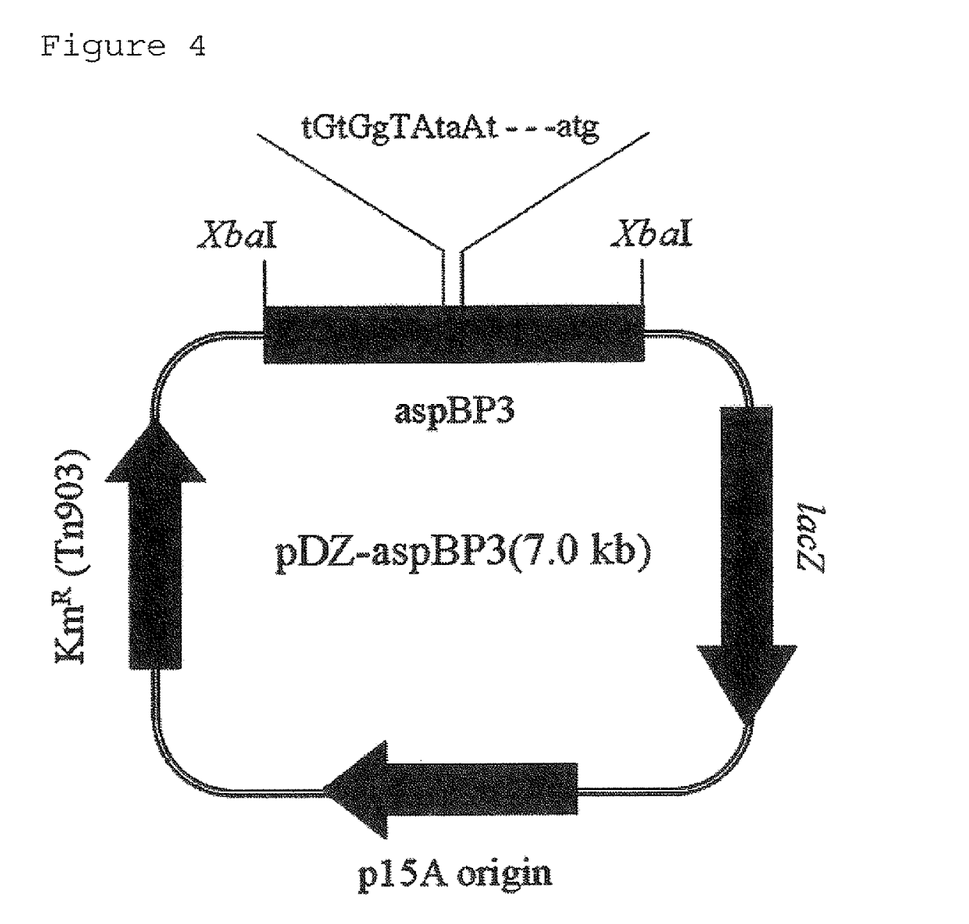
FIG. 4 shows a vector pDZ-aspBP3 for base substitution into *Corynebacterium*.

In one specific Example of the present invention, the present inventors constructed a vector capable of replacing the promoter region of aspB gene of *Corynebacterium glutamicum* with the mutated promoter sequence for improvement of its activity via homologous recombination. First, an *E. coli* cloning vector pACYC177 was treated with restriction enzymes to prepare blunt-ends, and for insertion of a lacZ gene, the lacZ gene was prepared by gene amplification from the genomic DNA of *E. coli* K12 W3110 through PCR, designed to contain the promoter thereof, followed by inserting an adaptor sequence containing a plurality of restriction enzyme recognition sites to construct the vector pDZ for the insertion into *Corynebacterium* chromosome (FIG. 1). Afterwards, as described above, the nucleic acid molecule having a high promoter activity, which is prepared to contain mutations in the promoter sequence of aspB gene, was inserted into the adapter region of the pDZ vector so as to construct a vector pDZ-aspBP1 containing the nucleic acid sequence of SEQ ID NO. 2 (FIG. 2), a vector pDZ-aspBP2 containing the nucleic acid sequence of SEQ ID NO. 3 (FIG. 3), and a vector pDZ-aspBP3 containing the nucleic acid sequence of SEQ ID NO. 4 (FIG. 4).

In still another aspect, the present invention relates to a transformant transformed with the vector.

The term "transformation", as used herein, means the introduction of DNA into a host in such a way that it can replicate either as an extrachromosomal element or by chromosomal integration. In one preferred embodiment, after transformation of a host cell with the vector, the nucleic acid sequence having a promoter activity within the vector may be integrated into the chromosome via homologous recombination with the promoter region of endogenous aspB gene on the host genome or retained in a plasmid form.

The transformation method of the vector of the present invention may include any method of introducing a nucleic acid into a cell, and may be performed by using suitable standard techniques known in the art, depending on the host cell. Examples thereof include electroporation, calcium phosphate ($CaPO_4$) precipitation, calcium chloride ($CaCl_2$) precipitation, microinjection, a polyethylene glycol (PEG) method, a DEAE-dextran method, a cationic liposome method, and an acetic acid lithium-DMSO method.

Host cells having high introduction efficiency of foreign DNA and having high expression levels of introduced DNA may be typically used as the host cells. Useful host cells may be all microorganisms including prokaryotic or eukaryotic cells, preferably *E. coli* or coryneform bacteria, more preferably the genus *Corynebacterium* or *Brevibacterium*, and much more preferably *Corynebacterium glutamicum* KFCC10881.

The transformant transformed with the vector of the present invention is characterized by having an aspB gene which has an enhanced promoter by replacement of the promoter region of the aspB gene of *Corynebacterium glutamicum* with the promoter sequence mutated to have an enhanced promoter activity through homologous recombination, thereby providing a higher aspartate aminotransferase activity than the wild-type.

In one specific Example of the present invention, each of the vector pDZ-aspBP1 containing the nucleic acid molecule having the promoter activity of SEQ ID NO. 2 (FIG. 2), the vector pDZ-aspBP2 containing the nucleic acid molecule having the promoter activity of SEQ ID NO. 3 (FIG. 3), and the vector pDZ-aspBP3 (FIG. 4) containing the nucleic acid molecule having the promoter activity of SEQ ID NO. 4 according to the present invention was transformed into *Corynebacterium glutamicum* KFCC10881 to prepare each transformant having an enhanced aspB promoter activity. In the present invention, a transformant transformed with pDZ-aspBP1, a transformant transformed with pDZ-aspBP2, and a transformant transformed with pDZ-aspBP3 were designated as KFCC10881-aspBP1, KFCC10881-aspBP2, and KFCC10881-aspBP3, respectively. The aspartate aminotransferase activity of each transformant was compared to that of the parental strain, KFCC10881. It was found that each transformant had 2.1, 2.6, and 1.8-fold higher activity than the parental strain (Table 3), indicating that the enhanced promoter of the present invention improves the aspartate aminotransferase activity. In addition, since the transformants were proved to have an effect of improving the activity, each of KFCC10881-aspBP1, KFCC10881-aspBP2, and KFCC10881-aspBP3 was designated as CA01-773, CA01-774, and CA01-775, and deposited at the Korean Culture Center of Microorganisms (hereinbelow, abbreviated to "KCCM") on Feb. 5, 2010 under the accession numbers, KCCM11061P, KCCM11062P and KCCM11063P.

In still another aspect, the present invention relates to a method for producing lysine comprising the step of culturing the transformant.

In the present invention, the cultivation of the transformants may be performed according to ordinary methods in the art, and the conditions such as temperature, time and pH of medium may be suitably controlled. The known cultivation methods are described in literature in the art [Chmiel; Bioprozesstechnik 1. Einfuhrung in die Bioverfahrenstechnik (Gustav Fischer Verlag, Stuttgart, 1991), and Storhas; Bioreaktoren und periphere Einrichtungen (Vieweg Verlag, Braunschweig/Wiesbaden, 1994)]. In addition, the cultivation methods include batch culture, continuous culture, and fed-batch culture. Preferably, the microorganisms may be continuously cultivated by the batch process, the fed batch process or the repeated fed batch process, but the methods are not limited thereto.

Culture media used for the cultivation need to meet requirements for growth of particular strains in an appropriate manner. Culture media for various strains are disclosed in, for example, "Manual of Methods for General Bacteriology" from American Society for Bacteriology (Washington D.C., USA, 1981). A carbon source for the culture media may be sugar and carbohydrate (e.g., glucose, sucrose, lactose, fructose, maltose, molasses, starch and cellulose), oil and fat (e.g., soybean oil, sunflower oil, peanut oil and coconut oil), a fatty acid (e.g., palmitic acid, stearic acid and linolenic acid), an alcohol (e.g., glycerol and ethanol), and an organic acid (e.g., acetic acid). The carbon sources may be used alone or in a mixture. A nitrogen source may also be a nitrogen-containing organic compound (e.g., peptone, yeast extract, meat extract, malt extract, corn steep liquor, soy meal and urea) or an inorganic compound (e.g., ammonium sulfate, ammonium chloride, ammonium phosphate, ammonium carbonate and ammonium nitrate). The nitrogen source may be used alone or in a mixture. A phosphorous source may be potassium dihydrogen phosphate, dipotassium hydrogen phosphate or its sodium salt thereof. In addition, the culture media should contain a metal salt (e.g., magnesium sulfate or iron sulfate) essential for growth. Finally, the culture medium may further include substances essential for growth such as amino acids and vitamins in addition to the above mentioned substances. Suitable precursors may be also added to the culture media. Those components of culture media may be added to the culture media on a batch or continuous basis during the cultivation.

The pH of the culture medium may be adjusted with a basic compound (e.g., sodium hydroxide, potassium hydroxide or ammonia), or an acidic compound (e.g., phosphoric acid or sulfuric acid). A defoaming agent such as fatty acid polyglycol ester may be added to prevent the formation of bubbles. An aerobic state may be maintained by injecting oxygen or oxygen-containing gas (e.g., air) into the culture medium. While the organism is cultured, the culture medium is typically maintained within the range from 20 to 45° C., and preferably within the range from 25 to 40° C. The culturing is continued until the production of L-amino acid reaches the maximum. In this regard, it takes 10 to 160 hours to attain the maximal amount of L-lysine. This amino acid may be released into the culture medium or may remain within the cells.

Meanwhile, the method for producing lysine comprising the step of culturing the transformant of the present invention may further comprise the step of recovering lysine that is produced in the above culturing step. The recovery of L-lysine from cells or culture media is well known in the art. Examples of L-lysine recovery methods include, but are not limited to, filtration, anion exchange chromatography, crystallization and HPLC.

MODE FOR INVENTION

In the present Examples, the transcriptional start site of aspB gene was identified for the construction of the enhanced promoter, and a recombinant vector for replacement of the aspB promoter of the lysine-producing strain *Corynebacterium glutamicum* with the enhanced promoter through homologous recombination was constructed. The vector was transformed into the *Corynebacterium glutamicum* KFCC10881 strain to obtain a strain having an enhanced promoter on the chromosome, whereby the strain produces lysine with high efficiency.

The *Corynebacterium glutamicum* KFCC10881 strain used in the present invention is a strain with resistance to S-(2-aminoethyl) cysteine (AEC) and a homoserine leaky character, which was prepared by artificial mutation of the wild-type *Corynebacterium glutamicum* strain (ATCC13032) as a parental strain (see Korean Patent Nos. 0159812 and 0397322).

Hereinafter, the present invention will be described in more detail with reference to the following Examples. However, these Examples are for illustrative purposes only, and the invention is not intended to be limited by these Examples.

Example 1

Identification of Transcriptional Start Site of aspB Gene

In the present Example, the unknown transcriptional start site of aspB gene was identified.

To identify the transcriptional start site of aspB gene, 5'-RACE (Rapid Amplification of 5' cDNA Ends) technique (Sambrook, J., Russell, D. W. Molecular Cloning: a laboratory manual $3^{rd}$ ed. 8.54) was performed. 5'-RACE is a method for cloning an unknown 5'-upstream region using a known mRNA, and was performed using a 5'-Full Race core set (Cat. No. 6122) available from Takara.

For the 5'-RACE experiment, five primers (Table 1, SEQ ID NOs. 5 to 9) were synthesized on the basis of the base sequence of aspB gene (NCBI Registration No. NCgl0237) registered in GenBank of the US National Institutes of Health (NIH).

TABLE 1

| Primer | Base sequence | SEQ ID NO. |
|---|---|---|
| aspB (race)/ RT | P-ccaagacctgctcc (5'-phosphorylated) | 5 |
| aspB (race)/ F1 | Tactcgcggtaagccttcg | 6 |
| aspB (race)/ R1 | Cttgagctcatcaaacttgc | 7 |
| aspB (race)/ F2 | Gatttcgctgatgagttgttg | 8 |
| aspB (race)/ R2 | Gcttaatgtcctcgtggaac | 9 |

First, mRNA was extracted from the strain ATCC 13032, and a $1^{st}$ strand cDNA was synthesized using a 5' end-phosphorylated RT-primer (SEQ ID NO. 5) specific to mRNA of the aspB gene by reverse transcription reaction. Subsequently, the RNA strand of hybrid DNA-RNA was degraded by RNaseH treatment, and then a single strand cDNA was circularized by RNA Ligase (or joined into a concatemeric form).

After completion of the ligation, PCR was performed using the sample as a template and SEQ ID NOs. 6 and 7 as a primer to obtain a primary PCR product. PCR was performed again using the primary PCR product as a template and SEQ ID NOs. 8 and 9 as a primer to obtain a secondary PCR product. PCR was performed under the following conditions: 30 cycles of denaturation at 95° C. for 30 sec; annealing at 55° C. for 30 sec; and polymerization at 72° C. for 1 min. Purification of the final PCR product was performed, and base sequence analysis was performed by sequencing.

As a result of the base sequence analysis, the transcriptional start site of the aspB gene was identified as G found 72 bp upstream of the initiation codon, ATG. The identified transcriptional start site was numbered as +1, and the promoter consensus sequence region was selected for improvement.

Example 2

Construction of Recombinant Vector for Promoter Improvement

<2-1> Construction of Vector for Chromosomal Insertion (pDZ)

In the present Example, on the basis of the *E. coli* cloning vector pACYC177 (New England Biolab, GenBank accession #X06402), a vector pDZ for the insertion into *Corynebacterium* chromosome was constructed.

The pACYC177 vector was treated with restriction enzymes, AcuI and BanI and then, klenow treatment was performed to yield blunt ends. The *E. coli*-derived lacZ gene to be used as a selection marker was amplified from genomic DNA of *E. coli* K12 W3110 by PCR, designed to include the promoter thereof, and treatment of T4 DNA polymerase and polynucleotide kinase was performed to create blunt ends and 5'-end phosphorylation. These two DNA fragments were ligated to each other to give a circular DNA molecule, followed by inserting an artificially synthesized adaptor sequence containing a plurality of restriction sites into the restriction site BamHI of the circular DNA molecule to construct the vector pDZ for insertion into *Corynebacterium* chromosome. FIG. 1 is a schematic view showing the vector pDZ for insertion into *Corynebacterium* chromosome.

<2-2> Construction of Recombinant Vector for Improvement of aspB Promoter

In the present Example, a recombinant vector was constructed in order to improve the promoter of the aspB gene derived from the lysine-producing strain, *Corynebacterium glutamicum*.

First, a base sequence (SEQ ID NO. 1) containing the promoter region of aspB gene (NCBI Registration No. NCgl0237) was acquired based on GenBank of the US National Institutes of Health (NIH), and DNA fragments containing the modified promoter sequences were obtained (SEQ ID NOs. 2, 3 and 4). Each modified promoter sequence was designed on the basis of the known promoter consensus sequence in general microorganism.

In addition, the eight primers (Table 2, SEQ ID NOs. 10 to 17) for the preparation of the modified promoter sequences were synthesized on the basis of the above base sequences;

TABLE 2

| Primer | Base sequence | SEQ ID NO. |
|---|---|---|
| aspB/PF | c cgg gga tcc tct aga ataggggatttgaaccctgag | 10 |
| aspB/PR | g cag gtc gac tct aga gccatagttacggacatcag | 11 |
| aspB/P1R | ag ccactatactaga cgttttaggggatccc | 12 |
| aspB/P1F | TCTA G TATAGT GG cttgaggtcactgctc | 13 |
| aspB/P2R | ag ccactatacCaCa cgttttaggggatccc | 14 |
| aspB/P2F | TGTG G TATAGT GG cttgaggtcactgctc | 15 |
| aspB/P3R | ag ccattatacCaCa cgttttaggggatccc | 16 |
| aspB/P3F | TGTG G TATAAT GG cttgaggtcactgctc | 17 |
| aspB/mut1 | CccctaaaacgtGtG | 18 |
| aspB/mut2 | CcctaaaacgtctagT | 19 |

Figure 2:
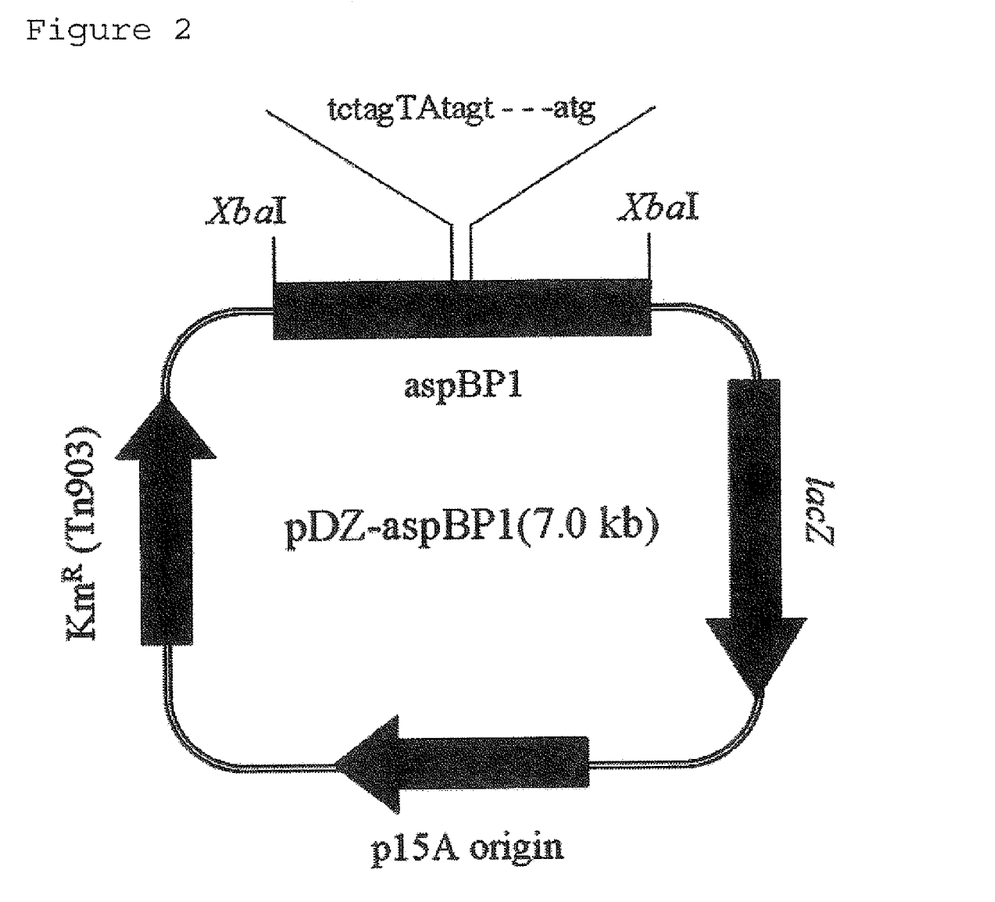
FIG. 2 shows a vector pDZ-aspBP1 for base substitution into *Corynebacterium*.

To obtain the promoter sequence of aspB gene derived from *Corynebacterium glutamicum*, PCR was performed using the chromosomal DNA of *Corynebacterium glutamicum* KFCC10881 as a template and the oligonucleotide pairs in Table 2 as a primer. A PfuUltra™ high-fidelity DNA polymerase was used as a polymerase and PCR conditions were as follows: 30 cycles of denaturation at 95° C. for 30 sec; annealing at 55° C. for 30 sec; and polymerization at 72° C. for 1 min. As a result, a DNA fragment of 300 bp containing the substituted region at one end was obtained. aspBP1-1 was amplified by using SEQ ID NOs. 10 and 12 as a primer, and aspBP1-2 was amplified by using SEQ ID NOs. 11 and 13 as a primer. The amplified product was mixed with the pDZ vector that was previously digested with XbaI restriction enzyme, and cloning was performed using an In-fusion Cloning Kit (TAKARA) to obtain a pDZ-aspBP1 vector.

pDZ-aspBP2 and pDZ-aspBP3 were also constructed in the same manner as in the preparation of pDZ-aspBP1, except that upon PCR amplification of insertion fragment, pDZ-aspBP2 was prepared from the aspBP2-1 fragment obtained using the primers of SEQ ID NOs. 10 and 14 and the aspBP2-2 fragment obtained using the primers of SEQ ID NOs. 11 and 15, and pDZ-aspBP3 was prepared from the aspBP3-1 fragment obtained using the primers of SEQ ID NOs. 10 and 16 and the aspBP3-2 fragment obtained using the primers of SEQ ID NOs. 11 and 17. FIGS. 2, 3, and 4 show the pDZ-aspBP1, pDZ-aspBP2, and pDZ-aspBP3 vectors for base substitution into *Corynebacterium*, each of them contains aspBP1, aspBP2, and aspBP3 corresponding to SEQ ID NOs. 2, 3 and 4, respectively.

Example 3

Insertion of Recombinant Vector into *Corynebacterium glutamicum* Strain

In the present Example, to improve the aspB promoter on the chromosome of *Corynebacterium*, the constructed recombinant vectors were transformed into the lysine-producing *Corynebacterium glutamicum* KFCC10881, and the promoter sequence on the chromosome was replaced with the promoter sequence of the vector by homologous recombination, leading to insertion of the enhanced promoter sequence into the chromosome.

Each of the recombinant vectors for base substitution into *Corynebacterium*, pDZ-aspBP1, pDZ-aspBP2 and pDZ-aspBP3, which were designed to include DNA fragments having the enhanced promoter sequences in Example 2, was transformed into *Corynebacterium glutamicum* KFCC10881 by an electrical pulse method (by transformation according to Appl. Microbiol. Biotechnol. (1999) 52:541-545), and screened for transformants, in which the gene of interest was inserted into the chromosome due to homology on a selection medium containing 25 mg/L of kanamycin.

The appearance of a blue color on the solid medium containing X-gal (5-bromo-4-chloro-3-indolyl-β-D-galactoside) indicated successful gene insertion into nuclear DNA using the vector. The primary chromosomal-inserted strains were cultured in a nutrient broth (30° C., 8 hrs) with shaking and were then serially diluted from $10^{-4}$ to $10^{-10}$ before being spread on solid media containing X-gal. Most of the colonies that were grown were stained a blue color. White colonies, which were a minority of the grown colonies, were selected. Strains having base substitution in the aspB promoter by secondary crossover were selected. These strains were finally analyzed for the base substitution and base sequence in the corresponding region through PCR before final selection.

The base substitution in the promoter was analyzed by PCR using the primers of SEQ ID NOs. 11 and 19, SEQ ID NOs. 11 and 18, and SEQ ID NOs. 11 and 18, each of them used for aspBP1, aspBP2 and aspBP3, and a final test was performed on the target region by base sequence analysis.

Finally, the lysine-producing strains, *Corynebacterium glutamicum* KFCC10881-aspBP1, KFCC10881-aspBP2, and KFCC10881-aspBP3, which have base substitution of the aspB promoter on the chromosome through secondary crossover, were obtained, and each of them was designated as CA01-773, CA01-774, and CA01-775, and deposited at the Korean Culture Center of Microorganisms on Feb. 5, 2010 under the accession numbers, KCCM11061P, KCCM11062P, and KCCM11063P.

Example 4

Assessment of Aspartate Aminotransferase Activity in Strain Having Enhanced aspB Promoter To assess aspartate aminotransferase activities of the parental strain *Corynebacterium glutamicum* KFCC10881 and the L-lysine-producing strains, *Corynebacterium glutamicum* KFCC10881-aspBP1, KFCC10881-aspBP2, and KFCC10881-aspBP3 that were finally prepared in Example 3, cultivation was performed as follows, and proteins were isolated from the culture media to assess the aspartate aminotransferase activity.

After each strain was cultured until the exponential phase was reached, the culture media was inoculated into 25 ml of the seed media to $OD_{600}$ of 0.3, followed by cultivation to approximately $OD_{600}$ of 15. The cells were collected from the culture media by centrifugation (5,000 rpm, 10 min), washed with 0.1% Tris-HCl buffer (pH 8.0) twice, and suspended in the same buffer to give the optical density at 600 nm of 160. 1.25 g of glass bead was added to 1.5 ml of suspension, and then the cells were disrupted using a bead beater for 6 min. The supernatant was collected by centrifugation (13,000 rpm, 30 min), and the protein concentration was determined by Bradford method (M.M 1976. Anal. Biochem. 72:248-254), and the supernatant was used as a crude protein solution for the assessment of aspartate aminotransferase activity.

The assessment of aspartate aminotransferase activity was initiated by addition of 0.1 ml of the crude protein solution to the reaction solution containing 0.24 M aspartate, 0.09 M Tris (pH7.8), 0.64 mM NADH, 0.11 mM pyridoxal phosphate, 0.93 kU/l MDH, and 0.42 kU/l LDH at 30° C. and 10 min, and then addition of 12 mM 2-oxoglutarate. The reduction in absorbance was measured at 340 nm for 5 min, followed by calculation of aspartate aminotransferase activity. One unit (U) of aspartate aminotransferase activity is defined as the reduced amount of NADH (nmole) by 1 mg of protein per minute.

Each aspartate aminotransferase activity of *Corynebacterium glutamicum* KFCC10881-aspBP1, KFCC10881-aspBP2 and KFCC10881-aspBP3 strains was compared with that of the parental strain, KFCC10881. As a result, it was found that KFCC10881-aspBP1, KFCC10881-aspBP2, and KFCC10881-aspBP3 strains showed 2.1, 2.6, and 1.8 fold-higher aspartate aminotransferase activities than the parental strain, respectively (Table 3).

TABLE 3

| Strain | Aspartate aminotransferase activity (U) | Folds |
|---|---|---|
| KFCC10881P | 196.5 | 1 |
| KFCC10881P-aspBP1 | 417.3 | 2.1 |
| KFCC10881P-aspBP2 | 517.1 | 2.6 |
| KFCC10881P-aspBP3 | 359.8 | 1.8 |

Seed Medium (pH 7.0)

raw sugar 20 g, peptone 10 g, yeast extract 5 g, urea 1.5 g, $KH_2PO_4$ 4 g, $K_2HPO_4$ 8 g, $MgSO_4$ $7H_2O$ 0.5 g, biotin 100 μg, thiamine HCl 1000 μg, calcium-pantothenic acid 2000 μg, nicotinamide 2000 μg (in 1 liter of distilled water)

Example 5

Lysine Production in Strain Having Enhanced aspB Promoter

For the production of L-lysine, *Corynebacterium glutamicum* KFCC10881 used as the parental strain and the L-lysine-producing strains, *Corynebacterium glutamicum* KFCC10881-aspBP1, KFCC10881-aspBP2, and KFCC10881-aspBP3 that were finally prepared in Example 3 were cultured as follows.

The parental strain *Corynebacterium glutamicum* KFCC10881, and KFCC10881-aspBP1, KFCC10881-aspBP2, and KFCC10881-aspBP3 were inoculated in a 250 ml corner-baffled flask containing 25 ml of the seed culture having the following composition, followed by culture at 30° C. for 20 hours with stirring at 200 rpm. 1 mL of the seed culture was inoculated in a 250 ml corner-baffled flask containing 24 ml of the production medium having the following composition, followed by culture at 30° C. for 120 hours with stirring at 200 rpm.

Upon completion of the culture, L-lysine production was measured by HPLC. The production amounts of L-lysine in the culture media of *Corynebacterium glutamicum* KFCC10881 and KFCC10881-aspBP1, KFCC10881-aspBP2, and KFCC10881-aspBP3 are shown in the following Table 4.

TABLE 4

| | Lysine (g/l) | | |
|---|---|---|---|
| Strain | Batch 1 | Batch 2 | Batch 3 |
| KFCC10881 | 43.5 | 44 | 43.7 |
| KFCC10881-aspBP1 | 45 | 45.8 | 45.4 |
| KFCC10881-aspBP2 | 45.6 | 46.5 | 46 |
| KFCC10881-aspBP3 | 44.8 | 45.5 | 45.4 |

Seed Medium (pH 7.0)

raw sugar 20 g, peptone 10 g, yeast extract 5 g, urea 1.5 g, $KH_2PO_4$ 4 g, $K_2HPO_4$ 8 g, $MgSO_4$ $7H_2O$ 0.5 g, biotin 100 μg, thiamine HCl 1000 μg, calcium-pantothenic acid 2000 μg, nicotinamide 2000 μg (in 1 liter of distilled water)

Production Medium (pH 7.0)

glucose 100 g, $(NH_4)_2SO_4$ 40 g, soy protein 2.5 g, corn steep solids 5 g, urea 3 g, $KH_2PO_4$ 1 g, $MgSO_4$ $7H_2O$ 0.5 g, biotin 100 μg, thiamine hydrochloride 1000 μg, calcium-pantothenic acid 2000 μg, nicotinamide 3000 μg, $CaCO_3$ 30 g (in 1 liter of distilled water)

As shown in the above Table 4, it was found that the KFCC10881-aspBP2 strain having 2.6-fold higher aspartate aminotransferase activity showed more than 5% increase of the lysine production, compared to the parental strain KFCC10881. It was also found that the KFCC10881-aspBP1 strain having 2.1-fold higher aspartate aminotransferase activity and the KFCC10881-aspBP3 strain having 1.8-fold higher aspartate aminotransferase activity showed more than 3% increase of the lysine production.

INDUSTRIAL APPLICABILITY

The nucleic acid molecule having enhanced promoter activity, derived from *Corynebacterium glutamicum*, according to the present invention, exhibits a higher promoter activity than the wild-type, thereby improving aspartate aminotransferase activity and the efficiency of lysine biosynthesis. Thus, L-lysine, which is one of L-amino acids useful in industry, can be produced with high efficiency.

What is claimed is:

1. A modified nucleic acid molecule having promoter activity comprising a nucleotide sequence selected from the group consisting of SEQ ID NOs.: 2, 3 and 4, wherein SEQ ID NO:2 is a modified SEQ ID NO: 1 having substitutions at positions 304 and 305, wherein Adenine at position 304 is substituted with Thymine, and Guanine at position 305 is substituted with Adenine, and wherein the nucleic acid molecule comprising SEQ ID NO:2 has enhanced promoter activity compared to the nucleic acid molecule of SEQ ID NO: 1.

2. The modified nucleic acid molecule according to claim 1, wherein the nucleic acid molecule is operably linked to a gene encoding aspartate aminotransferase.

3. A vector comprising the modified nucleic acid molecule having enhanced promoter activity of claim 1.

4. The vector according to claim 3, wherein the vector is pDZ-aspBP1 depicted in FIG. 2.

5. A transformant transformed with the vector of claim 3.

6. The transformant according to claim 5, wherein the transformant belongs to the genus *Corynebacterium* or *Brevibacterium*.

7. The transformant according to claim 5, wherein the transformant is identified by accession number of KCCM11061P.

8. The transformant according to claim 5, wherein the modified nucleic acid molecule having promoter activity is inserted into the chromosome by homologous recombination.

9. The transformant according to claim 5, wherein the modified nucleic acid molecule having promoter activity is retained in a plasmid form.

10. A method for producing lysine comprising the step of culturing the transformant of claim 5.

11. The method according to claim 10, wherein the method further comprises the step of recovering lysine that is produced in the above culturing step.

12. The modified nucleic acid molecule according to claim 1, wherein the modified nucleic acid molecule of SEQ ID NO:2 has further substitutions at positions 300 and 302, wherein Cytosine at position 300 is substituted with Guanine, and Adenine at position 302 is substituted with Guanine (SEQ ID NO:3).

13. The modified nucleic acid molecule according to claim 12, further comprising a substitution at positions 308, wherein Guanine at position 308 is substituted with Adenine (SEQ ID NO:4).

14. A vector comprising the modified nucleic acid molecule of claim 12.

15. A vector comprising the modified nucleic acid molecule of claim 13.

16. The vector according to claim 14, wherein the vector is pDZ-aspBP2 depicted in FIG. 3.

17. The vector according to claim 15, wherein the vector is pDZ-aspBP3 depicted in FIG. 4.

* * * * *

SEQUENCE LISTING

<160> NUMBER OF SEQ ID NOS: 19

<210> SEQ ID NO 1
<211> LENGTH: 608
<212> TYPE: DNA
<213> ORGANISM: Artificial Sequence
<220> FEATURE:
<223> OTHER INFORMATION: Nucleic acid sequence containing aspB promoter

<400> SEQUENCE: 1

```
atagggggatt tgaacccctg agggattgct cccaacccgc gttccaggcg agcgacatag      60
gccgctagtc gaatcctcca gctagaacgg ctgcaacgca tggctgcttt gttctgggga     120
ttagattaca caaaagtcgt ttagaaactc aaatccgctc gcagttggcg ttttctgggg     180
cggttcagct agagttatgc gaaggatccc gtgcggcgtt tatcttgtga actccccag      240
ggcaggaatg cagcaagggt cagcgagctc tgacgggtgc gcgggatccc ctaaaacgtc     300
tagagtagtg gcttgaggtc actgctcttt ttttgtgccc ttttttggtc cgtctatttt     360
gccaccacat gcggaggtac gcagttatga gttcagtttc gctgcaggat tttgatgcag     420
agcgaattgg tttgttccac gaggacatta agcgcaagtt tgatgagctc aagtcaaaaa     480
atctgaagct ggatcttact cgcggtaagc cttcgtcgga gcagttggat ttcgctgatg     540
agttgttggc gttgcctggt aagggtgatt tcaaggctgc ggatggtact gatgtccgta     600
actatggc                                                              608
```

<210> SEQ ID NO 2
<211> LENGTH: 608
<212> TYPE: DNA
<213> ORGANISM: Artificial Sequence
<220> FEATURE:
<223> OTHER INFORMATION: Nucleic acid sequence containing aspBP1 promoter

<400> SEQUENCE: 2

```
atagggggatt tgaacccctg agggattgct cccaacccgc gttccaggcg agcgacatag      60
gccgctagtc gaatcctcca gctagaacgg ctgcaacgca tggctgcttt gttctgggga     120
ttagattaca caaaagtcgt ttagaaactc aaatccgctc gcagttggcg ttttctgggg     180
cggttcagct agagttatgc gaaggatccc gtgcggcgtt tatcttgtga actccccag      240
ggcaggaatg cagcaagggt cagcgagctc tgacgggtgc gcgggatccc ctaaaacgtc     300
tagtatagtg gcttgaggtc actgctcttt ttttgtgccc ttttttggtc cgtctatttt     360
gccaccacat gcggaggtac gcagttatga gttcagtttc gctgcaggat tttgatgcag     420
agcgaattgg tttgttccac gaggacatta agcgcaagtt tgatgagctc aagtcaaaaa     480
atctgaagct ggatcttact cgcggtaagc cttcgtcgga gcagttggat ttcgctgatg     540
agttgttggc gttgcctggt aagggtgatt tcaaggctgc ggatggtact gatgtccgta     600
actatggc                                                              608
```

<210> SEQ ID NO 3
<211> LENGTH: 608
<212> TYPE: DNA
<213> ORGANISM: Artificial Sequence
<220> FEATURE:
<223> OTHER INFORMATION: Nucleic acid sequence containing aspBP2

-continued promoter

<400> SEQUENCE: 3

```
atagggatt tgaaccctg agggattgct cccaacccgc gttccaggcg agcgacatag      60
gccgctagtc gaatcctcca gctagaacgg ctgcaacgca tggctgcttt gttctgggga    120
ttagattaca caaaagtcgt ttagaaactc aaatccgctc gcagttggcg ttttctgggg    180
cggttcagct agagttatgc gaaggatccc gtgcggcgtt tatcttgtga actccccag     240
ggcaggaatg cagcaagggt cagcgagctc tgacgggtgc gcgggatccc ctaaaacgtg    300
tggtatagtg gcttgaggtc actgctcttt ttttgtgccc ttttttggtc cgtctatttt    360
gccaccacat gcggaggtac gcagttatga gttcagtttc gctgcaggat tttgatgcag    420
agcgaattgg tttgttccac gaggacatta agcgcaagtt tgatgagctc aagtcaaaaa    480
atctgaagct ggatcttact cgcggtaagc cttcgtcgga gcagttggat ttcgctgatg    540
agttgttggc gttgcctggt aagggtgatt tcaaggctgc ggatggtact gatgtccgta    600
actatggc                                                             608
```

<210> SEQ ID NO 4
<211> LENGTH: 608
<212> TYPE: DNA
<213> ORGANISM: Artificial Sequence
<220> FEATURE:
<223> OTHER INFORMATION: Nucleic acid sequence containing aspBP3
      promoter

<400> SEQUENCE: 4

```
atagggatt tgaaccctg agggattgct cccaacccgc gttccaggcg agcgacatag      60
gccgctagtc gaatcctcca gctagaacgg ctgcaacgca tggctgcttt gttctgggga    120
ttagattaca caaaagtcgt ttagaaactc aaatccgctc gcagttggcg ttttctgggg    180
cggttcagct agagttatgc gaaggatccc gtgcggcgtt tatcttgtga actccccag     240
ggcaggaatg cagcaagggt cagcgagctc tgacgggtgc gcgggatccc ctaaaacgtg    300
tggtataatg gcttgaggtc actgctcttt ttttgtgccc ttttttggtc cgtctatttt    360
gccaccacat gcggaggtac gcagttatga gttcagtttc gctgcaggat tttgatgcag    420
agcgaattgg tttgttccac gaggacatta agcgcaagtt tgatgagctc aagtcaaaaa    480
atctgaagct ggatcttact cgcggtaagc cttcgtcgga gcagttggat ttcgctgatg    540
agttgttggc gttgcctggt aagggtgatt tcaaggctgc ggatggtact gatgtccgta    600
actatggc                                                             608
```

<210> SEQ ID NO 5
<211> LENGTH: 14
<212> TYPE: DNA
<213> ORGANISM: Artificial Sequence
<220> FEATURE:
<223> OTHER INFORMATION: Primer for aspB(race)/RT, 5'-phosphorylated

<400> SEQUENCE: 5
ccaagacctg ctcc                                                      14

<210> SEQ ID NO 6
<211> LENGTH: 19
<212> TYPE: DNA
<213> ORGANISM: Artificial Sequence
<220> FEATURE:
<223> OTHER INFORMATION: Primer for aspB(race)/F1

<400> SEQUENCE: 6

```
tactcgcggt aagccttcg                                                   19

<210> SEQ ID NO 7
<211> LENGTH: 20
<212> TYPE: DNA
<213> ORGANISM: Artificial Sequence
<220> FEATURE:
<223> OTHER INFORMATION: Primer for aspB(race)/R1

<400> SEQUENCE: 7
cttgagctca tcaaacttgc                                                  20

<210> SEQ ID NO 8
<211> LENGTH: 21
<212> TYPE: DNA
<213> ORGANISM: Artificial Sequence
<220> FEATURE:
<223> OTHER INFORMATION: Primer for aspB(race)/F2

<400> SEQUENCE: 8
gatttcgctg atgagttgtt g                                                21

<210> SEQ ID NO 9
<211> LENGTH: 20
<212> TYPE: DNA
<213> ORGANISM: Artificial Sequence
<220> FEATURE:
<223> OTHER INFORMATION: Primer for aspB(race)/R2

<400> SEQUENCE: 9
gcttaatgtc ctcgtggaac                                                  20

<210> SEQ ID NO 10
<211> LENGTH: 38
<212> TYPE: DNA
<213> ORGANISM: Artificial Sequence
<220> FEATURE:
<223> OTHER INFORMATION: Primer for aspB/PF

<400> SEQUENCE: 10
ccggggatcc tctagaatag gggatttgaa cccctgag                              38

<210> SEQ ID NO 11
<211> LENGTH: 36
<212> TYPE: DNA
<213> ORGANISM: Artificial Sequence
<220> FEATURE:
<223> OTHER INFORMATION: Primer for aspB/PR

<400> SEQUENCE: 11
gcaggtcgac tctagagcca tagttacgga catcag                                36

<210> SEQ ID NO 12
<211> LENGTH: 31
<212> TYPE: DNA
<213> ORGANISM: Artificial Sequence
<220> FEATURE:
<223> OTHER INFORMATION: Primer for aspB/P1R

<400> SEQUENCE: 12
agccactata ctagacgttt taggggatcc c                                     31

<210> SEQ ID NO 13
<211> LENGTH: 29
<212> TYPE: DNA
<213> ORGANISM: Artificial Sequence
```

```
<220> FEATURE:
<223> OTHER INFORMATION: Primer for aspB/P1F

<400> SEQUENCE: 13
tctagtatag tggcttgagg tcactgctc                                29

<210> SEQ ID NO 14
<211> LENGTH: 31
<212> TYPE: DNA
<213> ORGANISM: Artificial Sequence
<220> FEATURE:
<223> OTHER INFORMATION: Primer for aspB/P2R

<400> SEQUENCE: 14
agccactata ccacacgttt taggggatcc c                             31

<210> SEQ ID NO 15
<211> LENGTH: 29
<212> TYPE: DNA
<213> ORGANISM: Artificial Sequence
<220> FEATURE:
<223> OTHER INFORMATION: Primer for aspB/P2F

<400> SEQUENCE: 15
tgtggtatag tggcttgagg tcactgctc                                29

<210> SEQ ID NO 16
<211> LENGTH: 31
<212> TYPE: DNA
<213> ORGANISM: Artificial Sequence
<220> FEATURE:
<223> OTHER INFORMATION: Primer for aspB/P3R

<400> SEQUENCE: 16
agccattata ccacacgttt taggggatcc c                             31

<210> SEQ ID NO 17
<211> LENGTH: 29
<212> TYPE: DNA
<213> ORGANISM: Artificial Sequence
<220> FEATURE:
<223> OTHER INFORMATION: Primer for aspB/P3F

<400> SEQUENCE: 17
tgtggtataa tggcttgagg tcactgctc                                29

<210> SEQ ID NO 18
<211> LENGTH: 15
<212> TYPE: DNA
<213> ORGANISM: Artificial Sequence
<220> FEATURE:
<223> OTHER INFORMATION: Primer for aspB/mut1

<400> SEQUENCE: 18
cccctaaaac gtgtg                                               15

<210> SEQ ID NO 19
<211> LENGTH: 16
<212> TYPE: DNA
<213> ORGANISM: Artificial Sequence
<220> FEATURE:
<223> OTHER INFORMATION: Primer for aspB/mut2

<400> SEQUENCE: 19
ccctaaaacg tctagt                                              16
```